US010758419B2

(12) United States Patent
Mirsepassi et al.

(10) Patent No.: US 10,758,419 B2
(45) Date of Patent: Sep. 1, 2020

(54) ILLUMINATED SURGICAL PROBE HAVING A VARIABLE ILLUMINATION NUMERICAL APERTURE

(71) Applicant: Novartis AG, Basel (CH)

(72) Inventors: Alireza Mirsepassi, Irvine, CA (US); Michael J. Papac, North Tustin, CA (US); Kambiz Parto, Laguna Niguel, CA (US)

(73) Assignee: Alcon Inc., Fribourg (CH)

( * ) Notice: Subject to any disclaimer, the term of this patent is extended or adjusted under 35 U.S.C. 154(b) by 355 days.

(21) Appl. No.: 15/813,472

(22) Filed: Nov. 15, 2017

(65) Prior Publication Data

US 2018/0168861 A1 Jun. 21, 2018

Related U.S. Application Data

(60) Provisional application No. 62/434,516, filed on Dec. 15, 2016.

(51) Int. Cl.
*A61F 9/00* (2006.01)
*A61F 9/009* (2006.01)
*A61F 9/007* (2006.01)
*A61F 9/008* (2006.01)
*A61B 90/30* (2016.01)
*A61B 3/00* (2006.01)
*A61B 3/13* (2006.01)

(52) U.S. Cl.
CPC .......... *A61F 9/009* (2013.01); *A61F 9/00736* (2013.01); *A61B 3/0008* (2013.01); *A61B 3/13* (2013.01); *A61B 2090/306* (2016.02); *A61F 9/0084* (2013.01); *A61F 2009/00874* (2013.01)

(58) Field of Classification Search
USPC ........................................................ 606/4–6
See application file for complete search history.

(56) References Cited

U.S. PATENT DOCUMENTS

| 5,651,783 | A | 7/1997 | Raynard |
| 5,916,149 | A | 6/1999 | Ryan, Jr. |
| 7,618,177 | B2 | 11/2009 | Cazzini |

(Continued)

FOREIGN PATENT DOCUMENTS

EP 1547550 A1 6/2005

OTHER PUBLICATIONS

Chalam, et al., Illuminated Curved Vitrectomy Probe for Vitreoretinal Surgery, Ophthalmic Surgery, Lasers and Imaging, Nov./Dec. 2007—vol. 38—Issue 6: 525-526.

(Continued)

*Primary Examiner* — Michael W Kahelin
*Assistant Examiner* — Shirley X Jian

(57) ABSTRACT

A surgical probe system comprising a surgical probe having a probe needle, an optical fiber incorporated onto the probe needle, wherein a proximal end of the optical fiber is connected to a light source and a distal end of the optical fiber projects illumination light from the light source over a tip of the probe needle; and an adjustment mechanism that varies the illumination light between a first beam having a first numerical aperture that facilitates vitreous visualization and a second beam having a second numerical aperture that facilitates background illumination, wherein the second numerical aperture is larger than the first numerical aperture.

20 Claims, 5 Drawing Sheets

(56) References Cited

U.S. PATENT DOCUMENTS

| | | |
|---|---|---|
| 7,783,346 B2 | 8/2010 | Smith et al. |
| 8,152,798 B2 | 4/2012 | Smith |
| 8,480,279 B2 | 7/2013 | Papac et al. |
| 8,485,972 B2 | 7/2013 | Papac et al. |
| 8,506,559 B2 * | 8/2013 | Raksi ............... A61F 9/00825 606/11 |
| 8,903,476 B2 | 12/2014 | Brennan et al. |
| 8,968,347 B2 | 3/2015 | McCollam |
| 9,017,316 B2 * | 4/2015 | Khatchaturov ...... A61N 5/0601 606/16 |
| 9,055,885 B2 | 6/2015 | Horvath |
| 9,072,587 B2 | 7/2015 | Smith |
| 9,089,364 B2 | 7/2015 | Bhadri |
| 9,364,982 B2 | 6/2016 | Schaller |
| 9,402,643 B2 | 8/2016 | Auld |
| 9,510,847 B2 | 12/2016 | Auld |
| 9,561,085 B2 | 2/2017 | Yadlowsky |
| 9,839,749 B2 | 12/2017 | Johnson |
| 9,956,053 B2 | 5/2018 | Diao |
| 10,016,248 B2 | 7/2018 | Mirsepassi |
| 10,068,173 B2 * | 9/2018 | Vayser ................ G02B 1/048 |
| 10,070,784 B2 | 9/2018 | Huang |
| 10,278,785 B2 | 5/2019 | Mirsepassi |
| 10,307,290 B2 | 6/2019 | Kern |
| 10,441,157 B2 | 10/2019 | Smith |
| 10,478,266 B2 | 11/2019 | Mirsepassi |
| 2005/0078910 A1 | 4/2005 | Hickingbotham |
| 2009/0182313 A1 | 7/2009 | Auld |
| 2011/0028951 A1 * | 2/2011 | Raksi ..................... A61F 9/008 606/4 |
| 2011/0118713 A1 * | 5/2011 | Raksi ................. A61F 9/00825 606/6 |
| 2013/0123769 A1 * | 5/2013 | Khatchaturov ...... A61N 5/0601 606/16 |
| 2014/0121469 A1 * | 5/2014 | Meckel ............... A61F 9/00821 600/249 |
| 2014/0276680 A1 * | 9/2014 | Dennison ........... A61F 9/00825 606/6 |
| 2015/0141972 A1 * | 5/2015 | Woodley ................ A61B 3/102 606/5 |
| 2017/0119491 A1 | 5/2017 | Mirsepassi |
| 2018/0055596 A1 | 3/2018 | Johnson |
| 2018/0133057 A1 | 5/2018 | Diao |
| 2018/0338776 A1 | 11/2018 | Farley |
| 2018/0338859 A1 | 11/2018 | Mirsepassi |
| 2018/0338860 A1 | 11/2018 | Farley |
| 2019/0209372 A1 | 7/2019 | Farley |
| 2019/0269556 A1 | 9/2019 | Meckel |
| 2019/0314111 A1 | 10/2019 | Lassalas |

OTHER PUBLICATIONS

Fisher et al., Inexpensive Illuminated Vitrectomy Cutter, The Journal of Retinal and Vitreous Diseases, Dec. 2003, vol. 23, Issue 6, p. 891.

Volpi International, The Universal Applicable Miniature Ringlight, Volpi International website, http://www.volpi.ch/htm/891/en/Miniature-Ringlight.htm; downloaded Jun. 29, 2012, 2 pages.

* cited by examiner

Incorporating an optical fiber onto the probe needle, wherein a proximal end of the optical fiber is connected to a light source and a distal end of the optical fiber projects illumination light from the light source over a tip of the probe needle.

41

Varying, by an adjustment mechanism, the illumination light between a first beam having a first numerical aperture that facilitates vitreous visualization and a second beam having a second numerical aperture that facilitates background illumination, wherein the second numerical aperture is larger than the first numerical aperture.

ILLUMINATED SURGICAL PROBE HAVING A VARIABLE ILLUMINATION NUMERICAL APERTURE

This application claims the benefit of priority of U.S. Provisional Patent Application Ser. No. 62/434,516 titled "Illuminated Surgical Probe Having a Variable Illumination Numerical Aperture", filed on Dec. 15, 2016, whose inventors are Alireza Mirsepassi, Michael J. Papac and Kambiz Parto, which is hereby incorporated by reference in its entirety as though fully and completely set forth herein.

BACKGROUND

In ophthalmic surgery, a surgeon may typically use a surgical apparatus comprising a vitreoretinal system with posterior segment and anterior segment procedure capabilities. The surgical apparatus may also include various probes, an ophthalmic microscope, an illuminator, a console with processors and a touch panel screen, and an embedded laser that's controlled from a system screen on the touch panel.

The types of probes used may include vitrectomy probes and laser probes. Vitrectomy probes may be used during vitreoretinal surgery to remove ocular tissues, such as vitreous humor and membranes covering the retina. These probes have a port for drawing in and dissecting tissues. A laser probe may have a continuous laser beam or a pulsed laser beam.

Some probe designs may include illumination that provides a narrow beam of light over the probe of sufficient intensity to facilitate vitreous visualization. However, the light beam can be too narrow and/or intense for certain tasks other than vitreous visualization. For example the narrow beam may be too intense for general illumination in the vitreous cavity or when the vitrectomy probe has to be operated very close to the retina for bi-manual surgery or other applications.

BRIEF SUMMARY

The exemplary embodiments provide methods and systems for a surgical probe system comprising a surgical probe having a probe needle, an optical fiber incorporated onto the probe needle, wherein a proximal end of the optical fiber is connected to a light source and a distal end of the optical fiber projects illumination light from the light source over tip of the probe needle; and an adjustment mechanism that varies the illumination light between a first beam having a first numerical aperture that facilitates vitreous visualization and a second beam having a second numerical aperture that facilitates background illumination, wherein the second numerical aperture is larger than the first numerical aperture.

According to the exemplary embodiments disclosed herein, an illuminated surgical probe having a variable illumination numerical aperture is provided.

BRIEF DESCRIPTION OF SEVERAL VIEWS OF THE DRAWINGS

FIG. 4 illustrates a method of providing an illuminated surgical probe having variable illumination numerical aperture.

DETAILED DESCRIPTION

The exemplary embodiment relates to an illuminated surgical probe having a variable numerical aperture. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

Figure 1A:
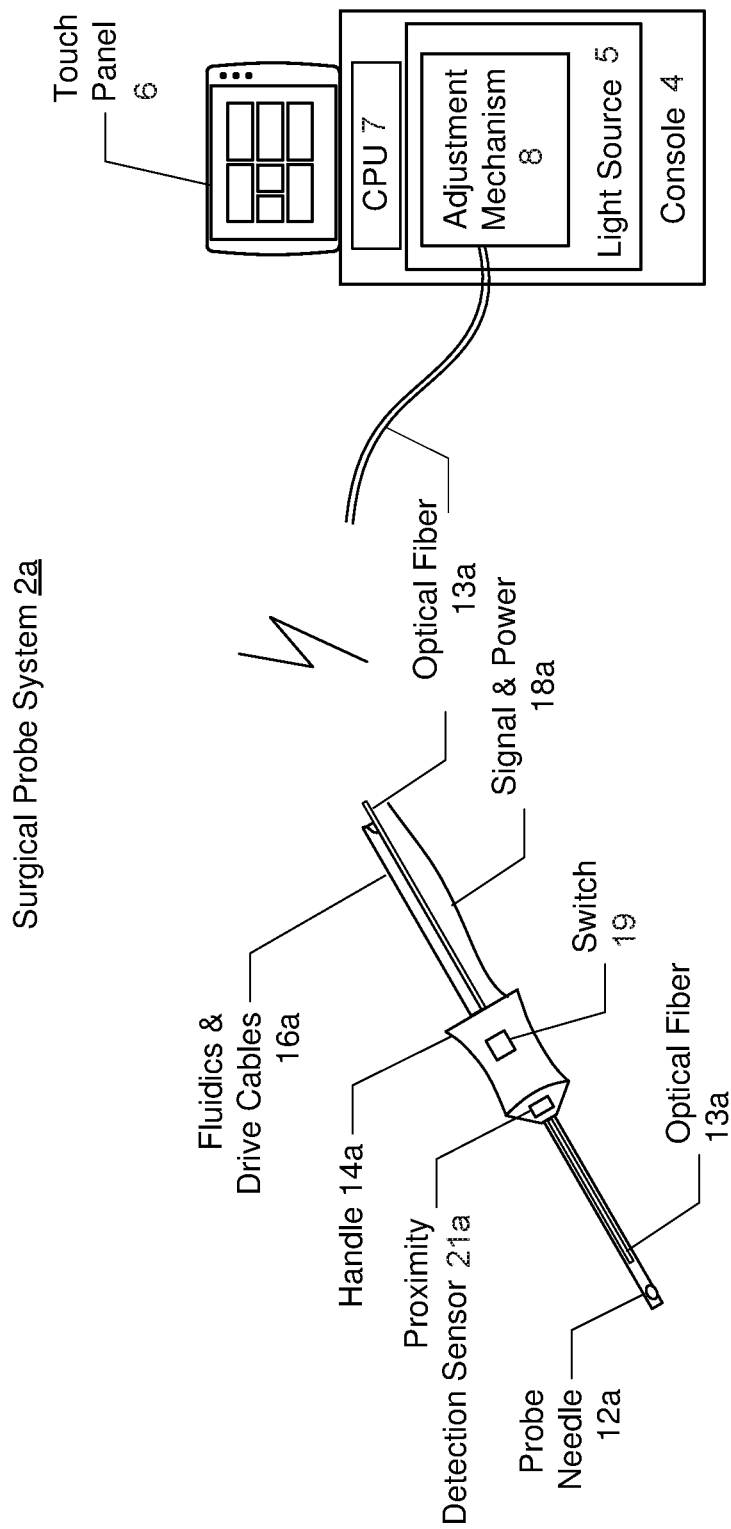
FIGS. 1A and 1B are diagrams illustrating embodiments of a surgical apparatus comprising an illuminated surgical probe having a variable numerical aperture, where like components have like reference numerals.
Figure 1B:
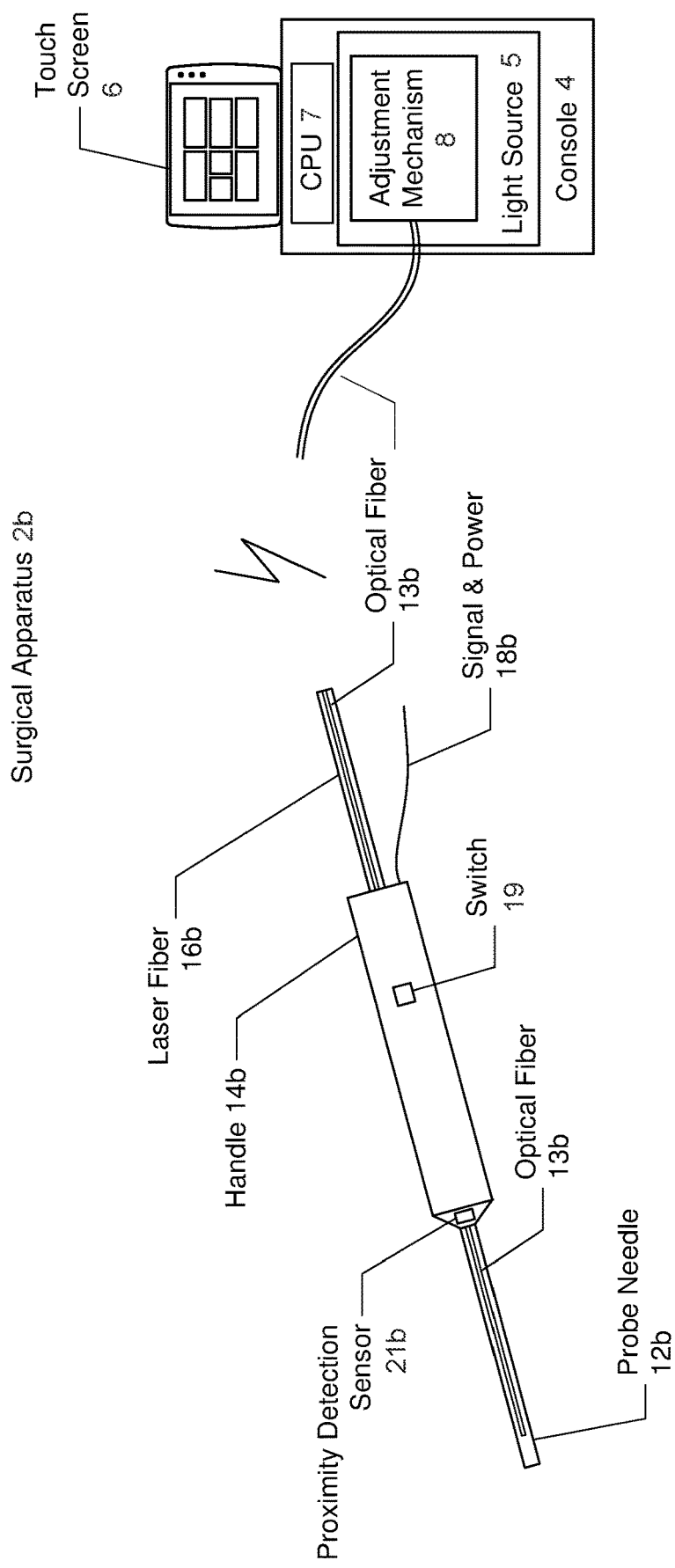

FIGS. 1A and 1B are diagrams illustrating embodiments of a surgical apparatus comprising an illuminated surgical probe having a variable numerical aperture, where like components have like reference numerals. FIG. 1A shows an embodiment where the surgical probe system 2a includes a hand-held surgical probe 10a coupled to console 4. In one embodiment, the surgical probe system 2a may represent a vitreoretinal system with posterior segment and anterior segment procedure capabilities. The console 4 of the surgical probe system 2a may include a light source (e.g., an illuminator) 5, a processor (e.g., CPU (Central Processing Unit)) 7, and a touch panel 6 that may be used to control the console 4a and the surgical probe 10a.

The surgical probe 10a may comprise a vitrectomy probe that includes a probe needle 12a connected to a handle 14a, which in turn, is connected to fluidics and drive cables 16a and a signal and power line 18a, both coupled to the console 4a. FIG. 1B shows an embodiment of a surgical probe system 2b where the surgical probe 10b comprises a laser probe, and similarly includes a probe needle 12b connected to a handle 14b, and the handle 14b connected to a laser fiber 16b and a signal and power line 18b.

According to one aspect of the exemplary embodiments, the surgical probe system 2a and 2b include an optical fiber 13a and 13b incorporated onto the probe needle 12a and 12b of the surgical probe 10a and 10b, respectively. Referring to both FIGS. 1A and 1B, a proximal end of the optical fiber 13 is connected to the light source 5 and a distal end of the optical fiber 13 projects illumination light from the light source 5 over tip of the probe needle 12. In addition, the surgical probe system 2 includes an adjustment mechanism 8 that varies the illumination light between a first beam having a first numerical aperture that facilitates vitreous visualization and a second beam having a second numerical aperture that facilitates background illumination, wherein the second numerical aperture is larger than the first numerical aperture.

Figure 2A:
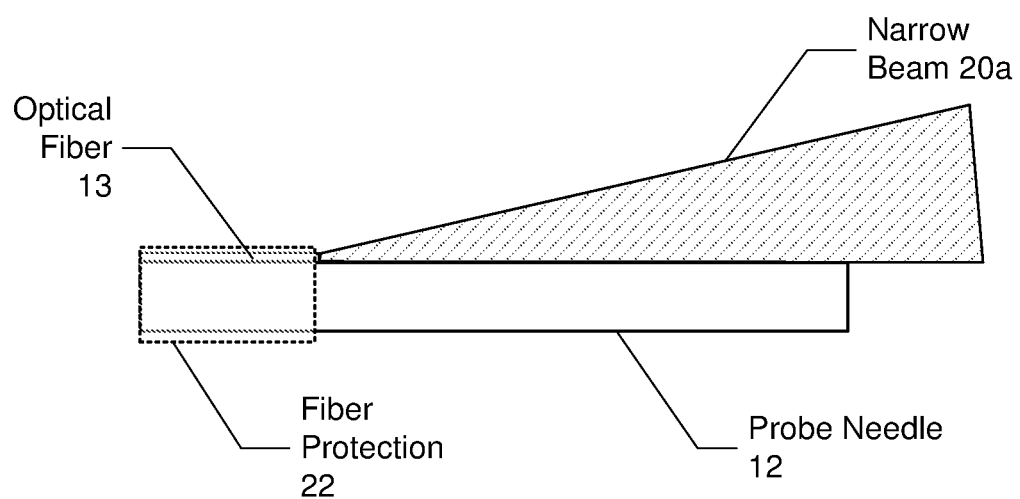
FIGS. 2A and 2B are diagrams illustrating first and second beams projected from the optical fiber as controlled by the adjustment mechanism
Figure 2B:
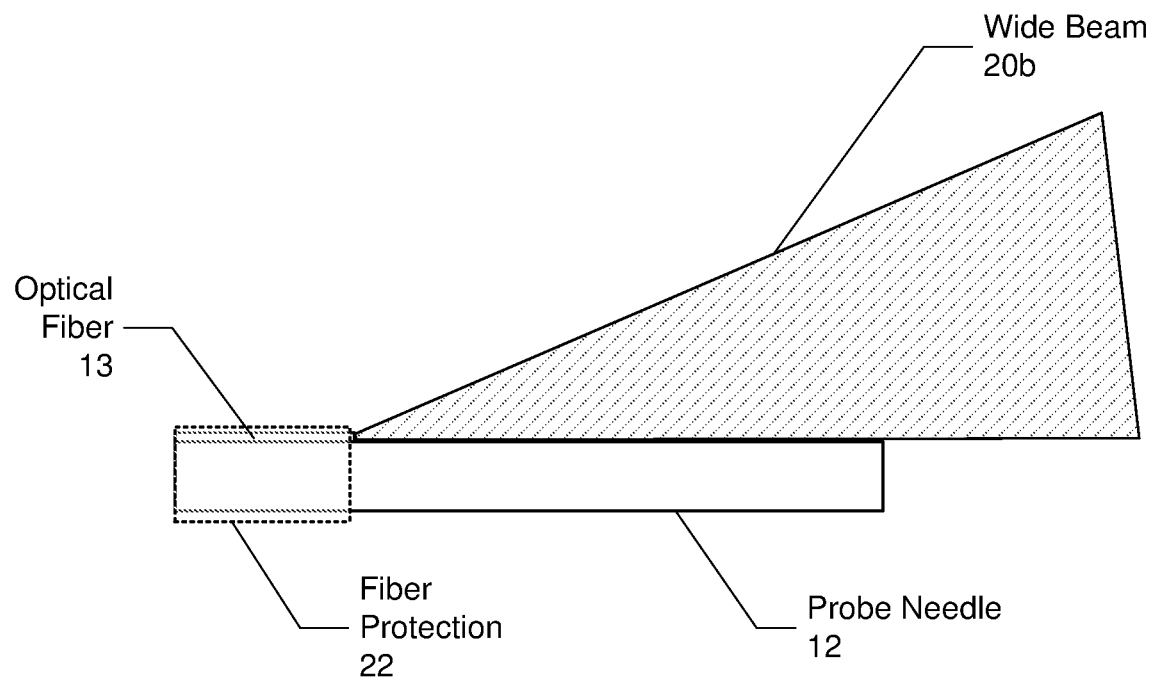

FIGS. 2A and 2B are diagrams illustrating first and second beams projected from the optical fiber as controlled by the adjustment mechanism 8. In one embodiment, the surgical probe 12 may further include optional fiber protection 22 that covers the optical fiber 13 and surrounds the portion of the probe needle 12 on which the optical fiber 13 lies. The fiber protection 22 may comprise any rigid material that supports and prevents crushing of the optical fiber 13. Example types of materials include stainless steel, glass, and the like.

In one embodiment, the adjustment mechanism 8 varies the illumination light between a narrow beam 20a and a wide beam 20b by changing a launch angle of the illumination light from the light source 5 into the proximal end of the optical fiber 13.

Referring to FIG. 2A, the adjustment mechanism 8 may adjust a launch angle of illumination light from the light source 5 into the proximal end of optical fiber 13 such that the narrow beam 20a of light with adequate intensity is delivered into the vitreous cavity for vitreous visualization. In one embodiment, the numerical aperture of the narrow beam has a low numerical value of approximately less than or equal to 0.3, or more specifically 0.1 to 0.3. In one specific application, the numerical aperture of the narrow beam may be 0.26.

Referring to FIG. 2B, the adjustment mechanism 8 may adjust a launch angle of illumination light from the light source 5 into the proximal end of optical fiber 13 such that a wide beam 20b is delivered into the vitreous cavity for general illumination (background illumination or task illumination, e.g., such as for membrane peeling). In one embodiment, the numerical aperture of the wide beam has a relatively high numerical value of approximately greater than 0.4, or more specifically 0.4 to 0.7. In one specific application, the numerical aperture of the wide beam may be 0.56.

Accordingly, the adjustment mechanism 8 provides background/situational awareness illumination by varying the numerical aperture of the light output. In one embodiment, the light launched into the fiber can be white light, a single wavelength (such as green light centered at 532 nm (nanometers)), RGB (Red Green Blue), or RGB plus additional wavelengths.

Figure 3A:
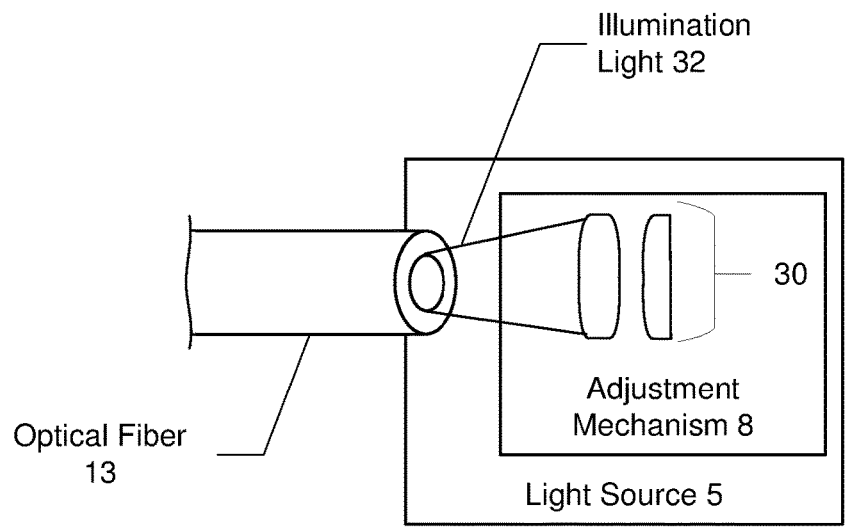
FIGS. 3A and 3B are diagrams illustrating implementation embodiments of the adjustment mechanism that controls the variable numerical aperture.
Figure 3B:
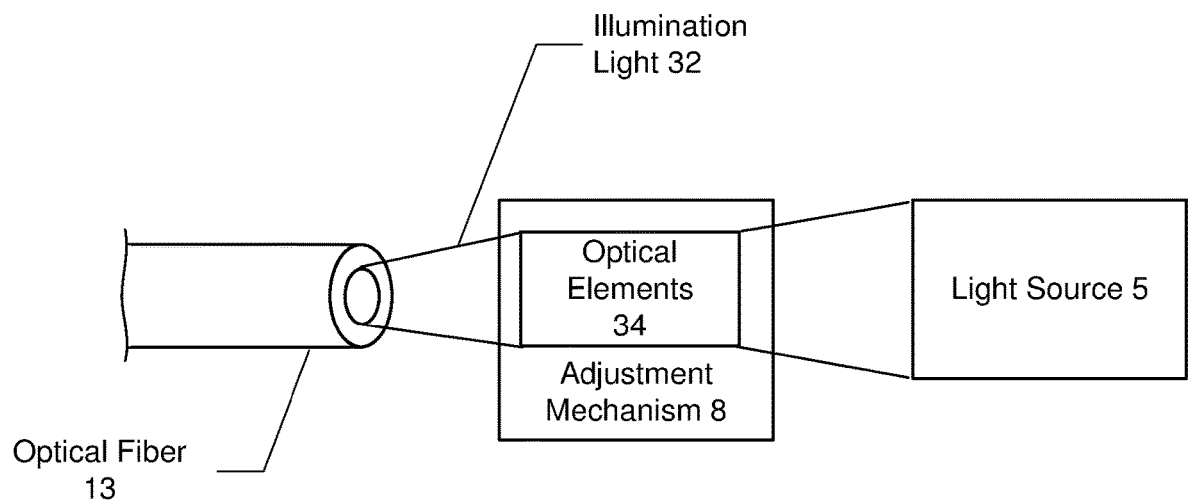

FIGS. 3A and 3B are diagrams illustrating implementation embodiments of the adjustment mechanism that controls the variable numerical aperture. FIG. 3A shows that in one embodiment, the adjustment mechanism 8 may comprise one or more lenses 30 incorporated in the light source 5 that focus illumination light 32 onto the optical fiber 13. In some embodiments, the adjustment mechanism may adjust the variable numerical aperture by moving the lenses relative to each other to adjust the light angle or by switching a light path between two different sets of lenses (each set configured to output the light at a different numerical aperture). Other adjustments of the numerical aperture are also contemplated.

FIG. 3B shows that in another embodiment, the adjustment mechanism 8 may comprise one or more optical elements 34 (e.g., lenses) placed in a path of the illumination light 32, prior to reaching the fiber, to disperse the illumination light 32 and change angular content of the illumination light 32. In some embodiments, the adjustment mechanism may adjust the variable numerical aperture by moving the optical elements relative to each other to adjust the light angle or by switching a light path between two different sets of optical elements (each set configured to output the light at a different numerical aperture). Other adjustments of the numerical aperture are also contemplated.

Referring again to FIGS. 1A and 1B, in one embodiment, the processor (CPU) 7 may be configured to control the adjustment mechanism 8 based on commands entered at the console 4 (e.g., through touch screen 6) to which the surgical probe 10 is connected. In another embodiment, the processor 7 may control the adjustment mechanism based on a command/signal received from a console to which the surgical probe is connected, a switch 19 on the surgical probe 10, and/or a footswitch. In one embodiment, the switch 19 may be located on the handle 14 of the surgical probe 10 and may comprise a two position switch, one position for the narrow beam and a second position for the wide beam. Other control mechanisms are also contemplated (e.g., instead of a switch, a dial on the surgical probe 10 may be rotated to change the numerical aperture). The numerical aperture may be changed in discrete increments (e.g., wide or narrow) or may be changed over a continuum.

In yet another embodiment, the processor 7 may control the adjustment mechanism 8 based on retinal proximity detection signals received from a retinal proximity detection sensor 21 (e.g., see proximity detection sensors 21a and 21b) that detects proximity or distance between the probe needle and a retina during surgery. Retinal proximity detection may be performed by an optical or ultrasonic retinal proximity detection sensor. In some embodiments, the processor 7 may switch the numerical aperture to a wide angle when the probe is located relatively close to the retina and to a narrow angle when the probe is located relatively far to the retina (for vitreous illumination). In some embodiments, the surgeon may program the relative distances at which the switching occurs. In some embodiments, the numerical aperture may be continuously changed (e.g., progressively widened or progressively narrowed) based on the detected distances. For example, as the probe gets further from the retina, the numerical aperture may become progressively narrowed. Further, as the probe gets closer to the retina, the numerical aperture may become progressively wider. Light intensity may also be controlled in a discrete or continuous matter by the processor and adjustment mechanism. For example, as the probe gets closer to the retina, the intensity of the light may be reduced. Further, as the probe gets further from the retina, the intensity of the light may be increased. In some embodiments, the type of light may also be adjusted by the processor and adjustment mechanism. For example, at further distances when a narrower numerical aperture is used, a white light may be used. Conversely, when the distance to the retina decreases and a wider numerical aperture is used, the adjustment mechanism may also filter out some of the frequencies of light introduced into the optical fiber. Other patterns of wider/narrow numerical aperture, light intensity used at various distances, and types of light at used various distances may be programmed by the surgeon (or preprogrammed) as needed.

In one embodiment, the retinal proximity detection sensor 21 may be located at any position of the surgical probe 10. Although in FIGS. 1A and 1B, the proximity sensor 21 is shown located within the handle 14 of the surgical probe 10, the proximity detection sensor 21 may be alternatively located along the probe needle 12 parallel to the optical fiber 13.

In an exemplary embodiment, the processor 7 is located in the console 4. However, in another embodiment, a processor used to control the adjustment mechanism 8 may be located within the surgical probe 10. In the embodiment where the processor is located within the surgical probe 10, a memory may be coupled to both the processor and the proximity sensor 21 or the switch 19 in the surgical probe 10. The memory 22 may be used to store the software instructions, as well as the data collected by the proximity sensor 21 and the data computed by the processor.

FIG. 4 illustrates a method of providing an illuminated surgical probe having variable illumination numerical aperture. The elements of FIG. 4 are meant to be illustrative. The elements may be performed in a different order and other elements may be added.

At 41, an optical fiber may be incorporated onto the probe needle, wherein a proximal end of the optical fiber is connected to a light source and a distal end of the optical fiber projects illumination light from the light source over a tip of the probe needle.

At 43, the illumination light may be varied, by an adjustment mechanism, between a first beam having a first numerical aperture that facilitates vitreous visualization and a second beam having a second numerical aperture that facilitates background illumination, wherein the second numerical aperture is larger than the first numerical aperture.

The processors 7 may be configured to execute the instructions stored in a memory to cause and control the process as described in this disclosure. As used herein, a processor may comprise one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality.

A method and system for an illuminated surgical probe having a variable numerical aperture has been disclosed. The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Accordingly, many modifications may be made by one of ordinary skill in the art without departing from the spirit and scope of the appended claims.

We claim:

1. A surgical probe system, comprising:
   a surgical probe having a probe needle;
   an optical fiber incorporated onto the probe needle, wherein a proximal end of the optical fiber is connected to a light source and a distal end of the optical fiber projects illumination light from the light source over a tip of the probe needle; and
   an adjustment mechanism that varies the illumination light between a first beam having a first numerical aperture that facilitates vitreous visualization and a second beam having a second numerical aperture that facilitates background illumination, wherein the second numerical aperture is larger than the first numerical aperture, wherein the first beam comprises a narrow beam, and the second beam comprises a wide beam;
   a retinal proximity detection sensor that detects proximity or distance between the surgical probe needle and a retina during surgery; and
   a processor configured to control the adjustment mechanism based on retinal proximity detection signals received from the retinal proximity detection sensor such that the processor switches to the first beam when the probe is located further than a first predetermined distance from the retina and switches to the second beam when the probe is located less than a second predetermined distance from the retina.

2. The surgical probe system as in claim 1, wherein the adjustment mechanism varies the illumination light between the first and second beams by changing a launch angle of the illumination light from the light source into the proximal end of the optical fiber.

3. The surgical probe system as in claim 1, wherein the first numerical aperture has a numerical value of approximately less than or equal to 0.3 and the second numerical aperture has a numerical value of approximately greater than 0.4.

4. The surgical probe system as in claim 1, wherein the adjustment mechanism comprises one or more lenses incorporated in the light source that focus the illumination light onto the fiber.

5. The surgical probe system as in claim 1, wherein the adjustment mechanism comprises one or more optical elements placed in a path of the illumination light, prior to reaching the optical fiber, to disperse the illumination light and change angular content of the illumination light.

6. The surgical probe system as in claim 1, wherein the processor is furthered configured to control the adjustment mechanism based on commands entered at a console to which the surgical probe is connected and a switch on the surgical probe.

7. The surgical probe system of claim 1, wherein the adjustment mechanism varies the illumination light between the first and second beams by switching a light path between two different sets of optical elements, each set configured to output a light at a different numerical aperture.

8. The surgical probe of claim 1, wherein the adjustment mechanism is further configured to change a type of light such that a white light is used for the first beam and the second beam has frequencies of light filtered out.

9. The surgical probe of claim 1, wherein the adjustment mechanism is further configured to change an intensity of light such that a lower intensity light is used for the second beam than the first beam.

10. The surgical probe system as in claim 1, wherein the processor is furthered configured to control the adjustment mechanism based on commands entered at a console to which the surgical probe is connected and a switch on the surgical probe.

11. A computer-implemented method of providing an illuminated surgical probe having variable illumination numerical aperture, the surgical probe comprising a probe needle, the method comprising:
   providing the probe needle with an optical fiber, wherein a proximal end of the optical fiber is connected to a light source and a distal end of the optical fiber projects illumination light from the light source over a tip of the probe needle;

detecting proximity to a retina using a retina proximity sensor;

varying, by an adjustment mechanism, the illumination light between a first beam having a first numerical aperture that facilitates vitreous visualization and a second beam having a second numerical aperture that facilitates background illumination, wherein the second numerical aperture is larger than the first numerical aperture and wherein the first beam comprises a narrow beam, and the second beam comprises a wide beam;

wherein varying the illumination light comprises switching to the first beam when the probe is located further than a first predetermined distance from the retina, based on input from the retinal proximity detection sensor, and switching to the second beam when the probe is located less than a second predetermined distance from the retina.

12. The method as in claim 11, wherein the adjustment mechanism varies the illumination light between the first and second beams by changing a launch angle of the illumination light from the light source into the proximal end of the optical fiber.

13. The method as in claim 11, wherein the first numerical aperture has a numerical value of approximately less than or equal to 0.3 and the second numerical aperture has a numerical value of approximately greater than 0.4.

14. The method as in claim 11, wherein the adjustment mechanism comprises one or more lenses incorporated in the light source that focus the illumination light onto the fiber.

15. The method as in claim 11, wherein the adjustment mechanism comprises one or more optical elements placed in a path of the illumination light, prior to reaching the optical fiber, to disperse the illumination light and change angular content of the illumination light.

16. The method as in claim 11, wherein the method further comprises controlling the adjustment mechanism based on commands entered at a console to which the surgical probe is connected and a switch on the surgical probe.

17. The method of claim 11, wherein the adjustment mechanism varies the illumination light between the first and second beams by switching a light path between two different sets of optical elements, each set configured to output a light at a different numerical aperture.

18. The method of claim 11, wherein switching between the first and second beam further comprises changing a type of light such that a white light is used for the first beam and frequencies of light are filtered out of the second beam.

19. The method of claim 11, wherein switching between the first and second beam further comprises changing an intensity of light such that a lower intensity light is used for the second beam than the first beam.

20. The method of claim 11, further comprising controlling the adjustment mechanism based on commands entered at a console to which the surgical probe is connected and a footswitch.

* * * * *